US012572627B2

(12) United States Patent
Sabeti et al.

(10) Patent No.: US 12,572,627 B2
(45) Date of Patent: Mar. 10, 2026

(54) SYSTEMS AND METHODS FOR ENHANCING ANOMALY DETECTION USING A PATTERN DICTIONARY

(71) Applicant: THE REGENTS OF THE UNIVERSITY OF MICHIGAN, Ann Arbor, MI (US)

(72) Inventors: Elyas Sabeti, Austin, TX (US); Alfred Hero, Ann Arbor, MI (US); Peter Song, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 830 days.

(21) Appl. No.: 17/898,711

(22) Filed: Aug. 30, 2022

(65) Prior Publication Data

US 2023/0074604 A1 Mar. 9, 2023

Related U.S. Application Data

(60) Provisional application No. 63/238,506, filed on Aug. 30, 2021.

(51) Int. Cl.
*G06F 18/28* (2023.01)
*A61B 5/00* (2006.01)
(Continued)

(52) U.S. Cl.
CPC ............ *G06F 18/28* (2023.01); *A61B 5/6802* (2013.01); *G06F 40/242* (2020.01); *G06F 40/289* (2020.01); *G06F 40/55* (2020.01)

(58) Field of Classification Search
CPC ........... A61B 5/01; A61B 5/021; A61B 5/024; A61B 5/0533; A61B 5/14542;
(Continued)

(56) References Cited

U.S. PATENT DOCUMENTS 9,489,582 B2 11/2016 Bala et al.
9,600,394 B2 3/2017 Salunke et al.
(Continued)

FOREIGN PATENT DOCUMENTS

CN 111694879 A 9/2020
CN 108776276 B 11/2020

OTHER PUBLICATIONS

J. Lin et al., "Rotation-invariant similarity in time series using bag-of-patterns representation"; Intell. Inf. Syst. 39, 287-315 (2012).
(Continued)

*Primary Examiner* — Amanda K Hulbert
(74) *Attorney, Agent, or Firm* — MARSHALL, GERSTEIN & BORUN LLP

(57) ABSTRACT

Systems and methods for enhancing anomaly detection using a pattern dictionary are disclosed. An example method includes receiving, from a wearable device, physiological data of the user, and parsing the physiological data into a set of parsed phrases having a number of parsed phrases by applying a pattern dictionary encoder using a pattern dictionary. Each parsed phrase represents a respective subsequence of the physiological data. The example method includes determining a codelength corresponding to the physiological data based on the set of parsed phrases, and comparing (i) the number of parsed phrases to a parsed phrase threshold, and (ii) the codelength to a codelength threshold using an anomaly detection model. Responsive to the number of parsed phrases exceeding the parsed phrase threshold or the codelength exceeding the codelength threshold, the example method includes generating an alert for display on a user interface indicating that the physiological data is anomalous.

12 Claims, 7 Drawing Sheets

(51) Int. Cl.
   *G06F 40/242*          (2020.01)
   *G06F 40/289*          (2020.01)
   *G06F 40/55*           (2020.01)

(58) Field of Classification Search
   CPC ... A61B 5/6802; A61B 5/7246; A61B 5/7275;
          A61B 5/742; G06F 18/28; G06F 2218/10;
              G06F 2218/12; G06F 40/211; G06F
                 40/242; G06F 40/289; G06F 40/55
   See application file for complete search history.

(56) References Cited

U.S. PATENT DOCUMENTS

| | | |
|---|---|---|
| 9,727,821 B2 | 8/2017 | Lin et al. |
| 9,801,562 B1 | 10/2017 | Host-Madsen |
| 10,061,677 B2 | 8/2018 | Toledano |
| 10,699,719 B1 | 6/2020 | Sieracki |
| 10,733,813 B2 | 8/2020 | Ide et al. |
| 2005/0138483 A1 | 6/2005 | Hatonen et al. |
| 2016/0371588 A1 | 12/2016 | Richardson et al. |
| 2020/0288983 A1 | 9/2020 | Telfort |
| 2020/0396249 A1 | 12/2020 | Shabtai et al. |

OTHER PUBLICATIONS

M. Kiermeier et al., "Anomaly Detection in Spatial Layer Models of Autonomous Agents"; Intl. Conf. on Intelligent Data Engineering and Automated Learning, 156-163 (2018).
S. U. Park et al., "A Physics-Based Pattern Dictionary for EBSD Image Segmentation"; Microscopy and Microanalysis 19, S2 (2013).
E. Sabeti et al., "Atyppicality for Heart Rate Variability Using a Pattern-Tree Weighting Method"; arXiv Preprint (2017.
A. Host-Madsen et al., "Coding of Graphs with Application to Graph Anomaly Detection"; 2018 IEEE International Symposium on Information Theory.

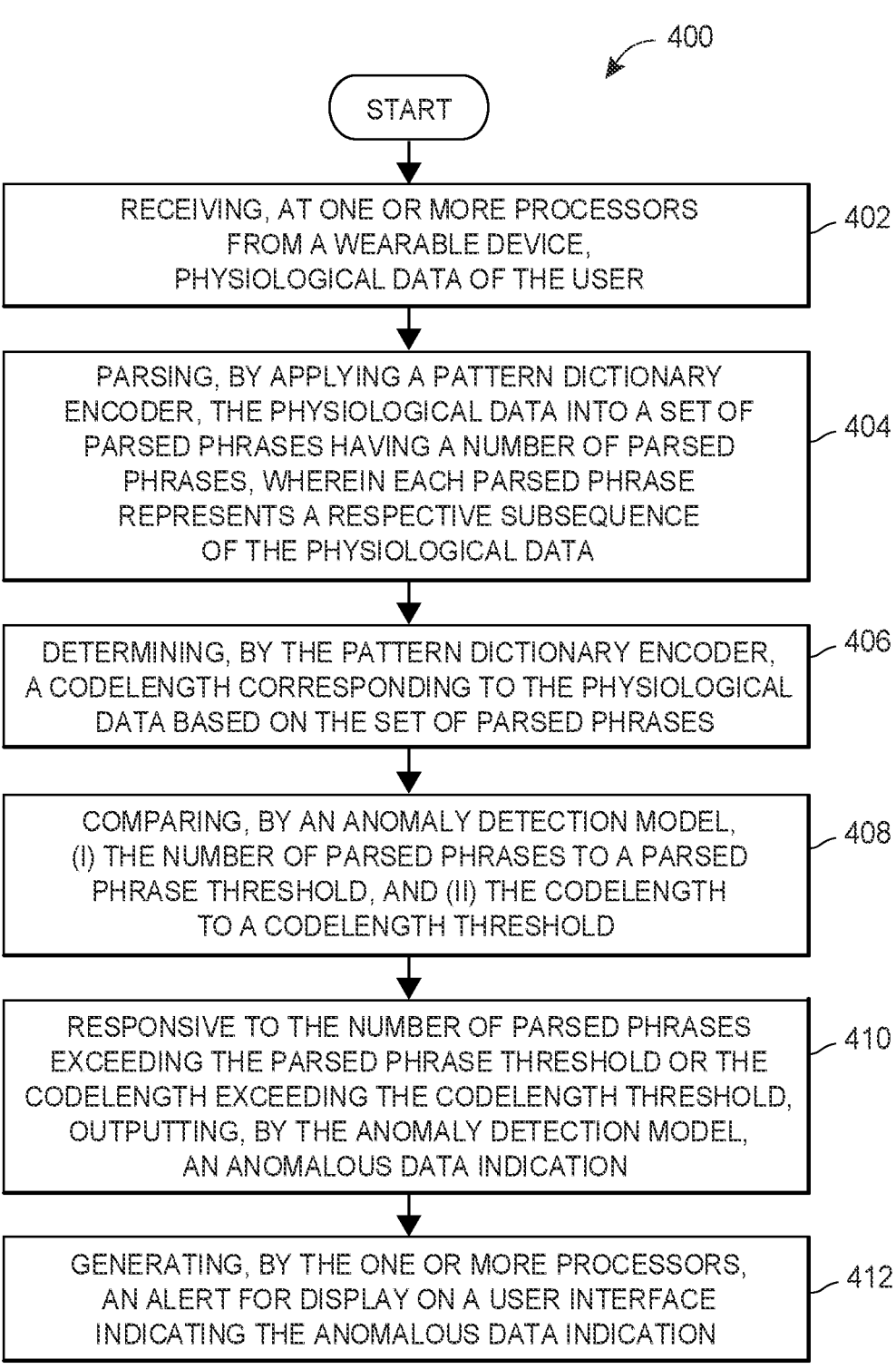

400

START

RECEIVING, AT ONE OR MORE PROCESSORS FROM A WEARABLE DEVICE, PHYSIOLOGICAL DATA OF THE USER — 402

PARSING, BY APPLYING A PATTERN DICTIONARY ENCODER, THE PHYSIOLOGICAL DATA INTO A SET OF PARSED PHRASES HAVING A NUMBER OF PARSED PHRASES, WHEREIN EACH PARSED PHRASE REPRESENTS A RESPECTIVE SUBSEQUENCE OF THE PHYSIOLOGICAL DATA — 404

DETERMINING, BY THE PATTERN DICTIONARY ENCODER, A CODELENGTH CORRESPONDING TO THE PHYSIOLOGICAL DATA BASED ON THE SET OF PARSED PHRASES — 406

COMPARING, BY AN ANOMALY DETECTION MODEL, (I) THE NUMBER OF PARSED PHRASES TO A PARSED PHRASE THRESHOLD, AND (II) THE CODELENGTH TO A CODELENGTH THRESHOLD — 408

RESPONSIVE TO THE NUMBER OF PARSED PHRASES EXCEEDING THE PARSED PHRASE THRESHOLD OR THE CODELENGTH EXCEEDING THE CODELENGTH THRESHOLD, OUTPUTTING, BY THE ANOMALY DETECTION MODEL, AN ANOMALOUS DATA INDICATION — 410

GENERATING, BY THE ONE OR MORE PROCESSORS, AN ALERT FOR DISPLAY ON A USER INTERFACE INDICATING THE ANOMALOUS DATA INDICATION — 412

FIG. 4

SYSTEMS AND METHODS FOR ENHANCING ANOMALY DETECTION USING A PATTERN DICTIONARY

CROSS-REFERENCE TO RELATED APPLICATIONS

This application claims the benefit of U.S. Provisional Application No. 63/238,506, filed Aug. 30, 2021, and entitled "SYSTEMS AND METHODS FOR ENHANCING ANOMALY DETECTION USING A PATTERN DICTION-ARY", which is incorporated herein by reference in its entirety.

FIELD OF THE DISCLOSURE

The present disclosure relates generally to techniques for detecting signal anomalies and, more particularly, to systems and methods for enhancing anomaly detection and using a pattern dictionary.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Infections and other adverse health conditions may cause a wide variety of deleterious effects to a patient's well-being. In certain cases, these adverse health conditions can produce debilitating symptoms and may cause lasting damage to a patient's health. For example, the global COVID-19 pandemic has infected millions across the planet, and causes a litany of symptoms including fever, shortness of breath, fatigue, congestion, nausea, and even loss of taste or smell. Unfortunately, many of these conditions can be highly contagious, and are potentially life-threatening to people of all ages if left undetected, untreated, and/or unmonitored.

Conventionally, there are numerous techniques for detecting and monitoring adverse health conditions. These techniques range from formal hospital settings that monitor patient vital signs using advanced medical technology to informal patient self-assessments. Problematically, each of these conventional techniques suffer from several drawbacks. Formal hospital settings and tests conducted therein are incredibly expensive and time-intensive, and the medical equipment itself generally lacks predictive power, leaving such analysis to the informed guesses of experienced physicians examining the results. By contrast, patient self-assessments generally provide underdeveloped views of a patient's health, which when combined with an average patient's lack of understanding of medical principles, can lead patients to underappreciate/neglect certain biological markers of infection and/or other adverse health conditions.

More recently, with the advances of physiological sensors integrated into consumer wearable devices, patients and/or medical providers may utilize the data from these wearables to assess a patient's general health. Most wearables include sensors capable of detecting a patient's heart rate, temperature, and activity level (most commonly in the form of steps taken). This data is easily accessible, and provides a relatively complete record of a patient's heart rate, temperature, and activity levels across days/weeks/months etc. As a result, consumer wearable device data has been integrated into several conventional techniques to provide useful insights related to a patient's cardiac health, daily activity levels, and other broad health indicators. However, this integration has not enabled the conventional techniques to evaluate a patient's risk of developing an adverse health condition with any greater effectiveness. In fact, utilizing this data as part of the conventional techniques (e.g., visiting a doctor) subjects the patient to many of the shortcomings associated with the conventional techniques (e.g., high prices, long wait times, general inconvenience) without use of the wearable consumer device data.

Many conventional data interpretation techniques are applied to interpret this wearable data, yet these techniques are unable to provide accurate adverse health condition prediction/analysis. Generally, conventional anomaly detection and outlier detection techniques are applied to wearable data in order to interpret the wearable data and predict adverse health conditions of the wearer. The wearable data collected by a user's wearable device is generally collected as a sequence or time series, such that any anomalous data contained therein may be characterized as a subsequence of the sequence or time series. However, the conventional anomaly/outlier detection techniques applied to interpret this wearable data typically fail to consider the sequential structure of the wearable data, and as a result, may improperly/inconsistently characterize the wearable data in a non-sequential manner.

Of course, anomaly detection is challenging due to the uncertain nature of anomalies, but this problem is more acutely expressed for wearable data because the length and occurrence frequency of potentially anomalous subsequences are unknown for time series and sequence data. Thus, the conventional anomaly/outlier detection techniques are notably deficient when attempting to interpret anomalous sequences from wearable data. Additionally, algorithmic computational complexity can provide a further challenge for conventional techniques, especially when the wearable data is received as a data stream with a large sequence alphabet.

Therefore, there is a need for techniques capable of accurately and efficiently detecting anomalous data sequences within data collected by a consumer wearable device to enhance the detection of adverse health conditions for users.

SUMMARY OF THE INVENTION

According to an aspect of the present disclosure, a system for enhancing anomaly detection using a pattern dictionary comprises a user interface, a wearable device of a user configured to capture physiological data of the user, a memory, and a processor interfacing with the wearable device, the memory, and the user interface. The memory stores a pattern dictionary and a set of computer-readable instructions comprising at least an anomaly detection model and a pattern dictionary encoder. The processor is configured to execute the set of computer-readable instructions to cause the processor to receive, from the wearable device, the physiological data of the user. The processor is further configured to parse, by the pattern dictionary encoder using the pattern dictionary, the physiological data into a set of parsed phrases having a number of parsed phrases, wherein each parsed phrase represents a respective subsequence of the physiological data; determine, by the pattern dictionary encoder, a codelength corresponding to the physiological data based on the set of parsed phrases; compare, by the anomaly detection model, (i) the number of parsed phrases to a parsed phrase threshold, and (ii) the codelength to a codelength threshold; responsive to the number of parsed phrases exceeding the parsed phrase threshold or the codelength exceeding the codelength threshold, output, by the anomaly detection model, an anomalous data indication; and generate an alert for display on the user interface indicating the anomalous data indication.

In certain arrangements, the set of set of computer-readable instructions further comprise a universal encoder, the codelength is a first codelength, and the set of computer-readable instructions further causes the processor to: determine, by the universal encoder, a second codelength corresponding to the physiological data, compare, by the anomaly detection model, the first codelength to the second codelength to determine a codelength deviation, and responsive to the codelength deviation exceeding a deviation threshold, generate, by the anomaly detection model, the alert.

In some arrangements, the set of computer-readable instructions further causes the processor to: receive, from the wearable device, a training data sequence corresponding to physiological signals of the user and an input from the user indicating a healthy physical condition of the user that is associated with the training data sequence, apply the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence, and input the training codelength value for each parsed phrase included in the pattern dictionary and the training number of parsed phrases into the anomaly detection model to train the anomaly detection model to output anomalous data indications. Further, in these arrangements, each parsed phrase included in the pattern dictionary and each parsed phrase included in the set of parsed phrases has a sequence length less than or equal to a maximum depth value associated with the pattern dictionary.

In certain arrangements, the system further comprises a server that is communicatively coupled with the user interface, the wearable device, the memory, and the processor. The server is configured to receive, from the processor via a network, the pattern dictionary, the set of parsed phrases, and an indication of whether or not the processor generated the alert, analyze the set of parsed phrases to identify a new parsed phrase that is not included in the pattern dictionary, responsive to determining that the indication indicates that the processor did not generate the alert, update the pattern dictionary by including the new parsed phrase in the pattern dictionary, and transmitting, to the processor via the network, the pattern dictionary including the new parsed phrase.

In some arrangements, the server is further configured to: receive, via the network, a plurality of respective physiological data corresponding to a plurality of respective individuals, wherein a respective physiological data of the plurality of respective physiological data includes a respective new parsed phrase, update the pattern dictionary by including the respective new parsed phrase in the pattern dictionary, and transmit, to the processor via the network, the pattern dictionary including the respective new parsed phrase.

In certain arrangements, the anomaly detection algorithm further causes the processor to: parse the physiological data into the set of parsed phrases by iteratively adjusting a string length and an initial string character of the physiological data that is analyzed by the pattern dictionary encoder until all subsequences comprising the physiological data that have a respective string length less than or equal to a maximum depth value are analyzed.

In some arrangements, the physiological data of the user includes at least one of: (i) a heart rate of the user, (ii) a temperature of the user, (iii) a blood pressure of the user, (iv) an electro dermal activity level of the user, (v) an inertial measurement unit (IMU) value of the user, or (vi) a blood oxygen level of the user.

According to another aspect of the present disclosure, a method for enhancing anomaly detection using a pattern dictionary encoder includes receiving, at one or more processors from a wearable device, physiological data of the user. The method further includes parsing, by applying a pattern dictionary encoder using a pattern dictionary, the physiological data into a set of parsed phrases having a number of parsed phrases, wherein each parsed phrase represents a respective subsequence of the physiological data; determining, by the pattern dictionary encoder, a codelength corresponding to the physiological data based on the set of parsed phrases; comparing, by an anomaly detection model, (i) the number of parsed phrases to a parsed phrase threshold, and (ii) the codelength to a codelength threshold; responsive to the number of parsed phrases exceeding the parsed phrase threshold or the codelength exceeding the codelength threshold, outputting, by the anomaly detection model, an anomalous data indication; and generating, by the one or more processors, an alert for display on a user interface indicating the anomalous data indication.

In some arrangements, the codelength is a first codelength, and the method further comprises: determining, by applying a universal encoder, a second codelength corresponding to the physiological data; comparing, by the anomaly detection model, the first codelength to the second codelength to determine a codelength deviation; and responsive to the codelength deviation exceeding a deviation threshold, generating, by the one or more processors, the alert.

In certain arrangements, the method further comprises: receiving, from the wearable device, a training data sequence corresponding to physiological signals of the user and an input from the user indicating a healthy physical condition of the user that is associated with the training data sequence; applying, by the one or more processors, the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence; and inputting, by the one or more processors, the training codelength value for each parsed phrase included in the pattern dictionary and the training number of parsed phrases into the anomaly detection model to train the anomaly detection model to output anomalous data indications. Further in these arrangements, each parsed phrase included in the pattern dictionary and each parsed phrase included in the set of parsed phrases has a sequence length less than or equal to a maximum depth value associated with the pattern dictionary.

In some arrangements, the method further comprises: receiving, at a server from the one or more processors via a network, the pattern dictionary, the set of parsed phrases, and an indication of whether or not the one or more processors generated the alert; analyzing, by the server, the set of parsed phrases to identify a new parsed phrase that is not included in the pattern dictionary; responsive to determining that the indication indicates that the one or more processors did not generate the alert, updating, by the server, the pattern dictionary by including the new parsed phrase in the pattern dictionary; and transmitting, from the server to the one or more processors via the network, the pattern dictionary including the new parsed phrase.

In certain arrangements, the method further comprises: receiving, at the server via the network, a plurality of respective physiological data corresponding to a plurality of respective individuals, wherein a respective physiological data of the plurality of respective physiological data includes a respective new parsed phrase; updating, by the server, the pattern dictionary by including the respective new parsed phrase in the pattern dictionary; and transmitting, to the one or more processors from the server via the network, the pattern dictionary including the respective new parsed phrase.

In some arrangements, the method further comprises: parsing, by applying the pattern dictionary encoder, the physiological data into the set of parsed phrases by iteratively adjusting a string length and an initial string character of the physiological data that is analyzed by the pattern dictionary encoder until all subsequences comprising the physiological data that have a respective string length less than or equal to a maximum depth value are analyzed.

According to yet another aspect of the present disclosure, a non-transitory computer-readable storage medium has stored thereon a set of instructions, executable by at least one processor, for enhancing anomaly detection using a pattern dictionary encoder. The instructions comprise instructions for receiving, from a wearable device, physiological data of the user; instructions for parsing, by applying a pattern dictionary encoder using a pattern dictionary, the physiological data into a set of parsed phrases having a number of parsed phrases, wherein each parsed phrase represents a respective subsequence of the physiological data; instructions for determining, by the pattern dictionary encoder, a codelength corresponding to the physiological data based on the set of parsed phrases; instructions for comparing, by an anomaly detection model, (i) the number of parsed phrases to a parsed phrase threshold, and (ii) the codelength to a codelength threshold; instructions for, responsive to the number of parsed phrases exceeding the parsed phrase threshold or the codelength exceeding the codelength threshold, outputting, by the anomaly detection model, an anomalous data indication; and instructions for generating an alert for display on a user interface indicating the anomalous data indication.

In some arrangements, the codelength is a first codelength, and the instructions further comprise: instructions for determining, by applying a universal encoder, a second codelength corresponding to the physiological data; instructions for comparing, by the anomaly detection model, the first codelength to the second codelength to determine a codelength deviation; and instructions for, responsive to the codelength deviation exceeding a deviation threshold, generating the alert.

In certain arrangements, the instructions further comprise: instructions for receiving, from the wearable device, a training data sequence corresponding to physiological signals of the user and an input from the user indicating a healthy physical condition of the user that is associated with the training data sequence; instructions for applying the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence; and instructions for inputting the training codelength value for each parsed phrase included in the pattern dictionary and the training number of parsed phrases into the anomaly detection model to train the anomaly detection model to output anomalous data indications.

In some arrangements, each parsed phrase included in the pattern dictionary and each parsed phrase included in the set of parsed phrases has a sequence length less than or equal to a maximum depth value associated with the pattern dictionary.

In certain arrangements, the instructions further comprise: instructions for parsing, by applying the pattern dictionary encoder, the physiological data into the set of parsed phrases by iteratively adjusting a string length and an initial string character of the physiological data that is analyzed by the pattern dictionary encoder until all subsequences comprising the physiological data that have a respective string length less than or equal to a maximum depth value are analyzed.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 4 illustrates an example method for enhancing anomaly detection using a pattern dictionary, in accordance various aspects disclosed herein.

DETAILED DESCRIPTION

Generally, wearable consumer devices (also referenced herein as "wearables" and "wearable devices") have emerged as a key tool in the fight against infections and many other adverse health conditions. Wearables provide a convenient, low-cost solution to obtain user-specific physiological data. Moreover, wearables may enable more frequent and more remote (e.g., at-home) monitoring of a user's health status, which can be crucial during periods before and during a user's adverse health condition. Using the systems and methods of the present disclosure, these wearables can accurately detect an adverse health condition and/or other anomalous condition based on a trained pattern dictionary and anomaly detection model.

Physiological signals that are measured by wearables, such as but not limited to heart rate, temperature, and steps, reflect the combined action of many physiological and environmental signals on a user's health. For example, circadian timekeeping, the effect of activity (e.g., steps) on heart rate and temperature, the effect of sleep, cortisol or other hormones, and the physiological effects of meals, drugs including caffeine and posture all play an important role in the resulting physiological signals measured by the wearable devices. As a result of these complex physiological effects, the signals measured by the wearable device may include many patterns/sequences that indicate the user's physiological systems are healthy and/or otherwise well-functioning. The systems and methods of the present disclosure generally parse the data collected by the wearable device into a number of parsed phrases using a trained pattern dictionary and pattern dictionary encoder, and additionally determine a codelength for these parsed phrases. Using the number of parsed phrases and the codelength, a trained anomaly detection model may determine whether or not any portion (e.g., subsequence) of the physiological data is anomalous. By parsing and analyzing the wearable data in this manner, the systems and methods of the present disclosure provide increased predictive power for detecting anomalous signals (e.g., adverse health conditions/events) compared to conventional techniques. Namely, the systems and methods of the present disclosure improve over conventional techniques by accurately classifying anomalous data sequences with an area under the curve (AUC) of approximately 0.91-0.96.

Moreover, these techniques can be used in home or clinical settings to identify suitable treatments or triage medical resources in a flexible manner that conventional techniques are incapable of providing. Of course, while described herein as identifying adverse health conditions, the techniques described herein are generally applicable to any suitable data set that may be characterized similarly to physiological data collected from a user's wearable device.

Figure 1A:
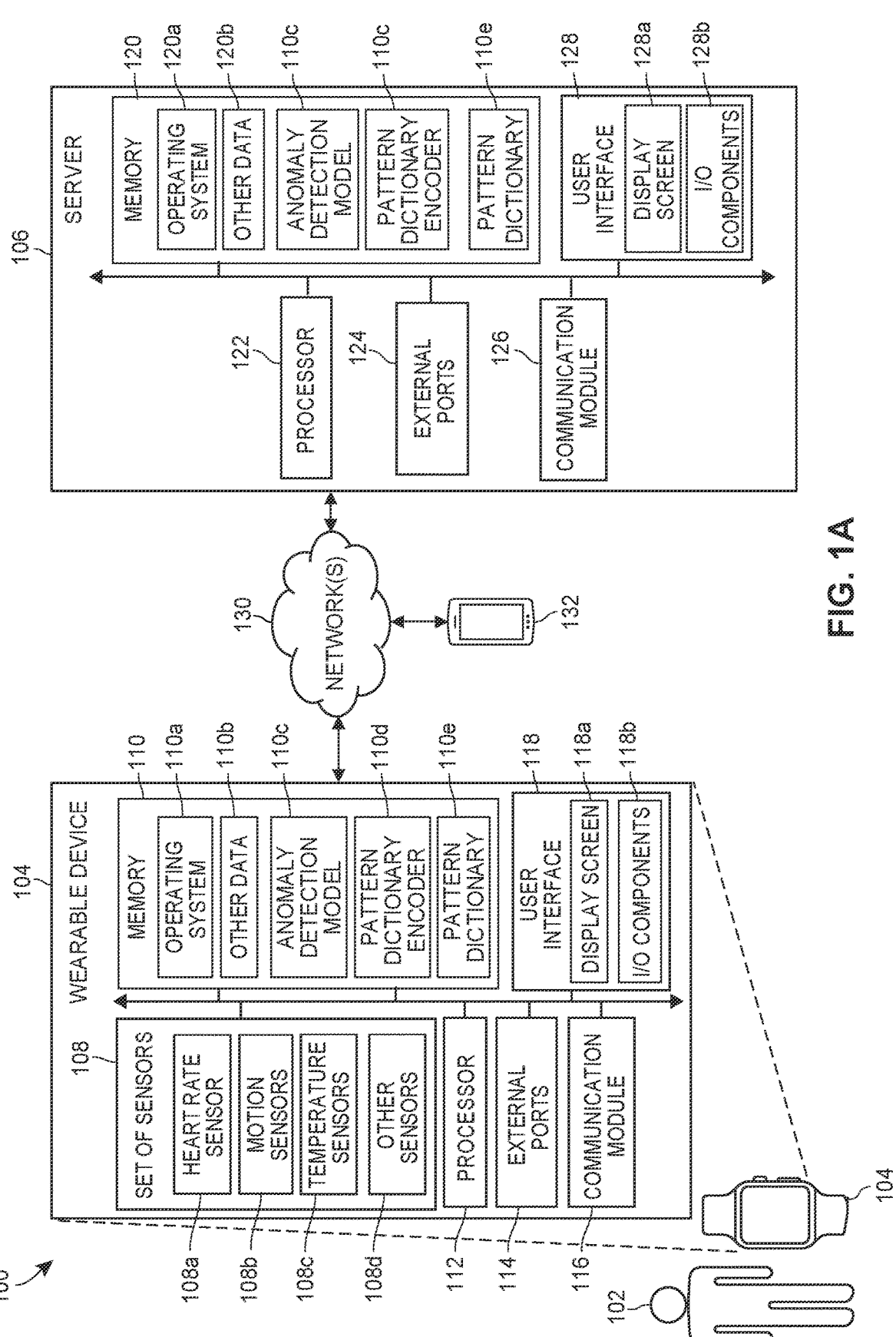
FIG. 1A illustrates an example system for enhancing anomaly detection using a pattern dictionary, in accordance various aspects disclosed herein.

FIG. 1A illustrates an example system 100 for enhancing anomaly detection using a pattern dictionary. It should be appreciated that the example system 100 is merely an example and that alternative or additional components are envisioned.

As illustrated in FIG. 1A, the example system 100 features a user 102 who may wear a wearable device 104 and a server 106. Generally, the wearable device 104 may be any device that is wearable by a user that is configured to monitor and collect physiological data corresponding to the user. For example, the wearable device 104 may be a smartwatch/bracelet (e.g., FITBIT, APPLE Watch, WHOOP Strap, etc.), smart ring, knee bands, arm bands, sensor patches, clothing-based monitors, chest straps, etc. The system 100 may also include other wearable devices which may be worn by the user 102, such as a smart ring in addition to a smartwatch (e.g., wearable device 104).

The wearable device 104 may include a set of sensors 108 that are each configured to detect and/or collect physiological data of the user 102. The set of sensors 108 may include a heart rate sensor 108a (e.g., an optical heart rate sensor)

that is configured to detect and collect heart rate data of the user 102, motion sensor(s) 108b configured to detect and collect motion data corresponding to the user 102, temperature sensors 108c configured to detect and collect temperature data corresponding to the user, and other sensors 108d. The motion sensor(s) 108b may include, for example, an inertial measurement unit (IMU) (comprising an accelerometer, a gyroscope, and a magnetometer), an altimeter, a global positioning system (GPS), an electrodermal activity (EDA) sensor, and/or any other suitable sensor or combinations thereof. The temperature sensors 108c may include any suitable temperature sensing device, such as a skin temperature sensor utilizing any of a negative temperature coefficient (NTC) thermistor, a resistance temperature detector (RTD), a thermocouple, a semiconductor-based sensor, and/or any other suitable temperature sensing device. The set of sensors 108 may also include other sensors 108c, such as an ultraviolet (UV) sensor, a gesture sensor, an electrocardiogram (ECG) sensor, a proximity sensor, a bioimpedance sensor, a pulse oximeter (Sp02) sensor, an ambient light sensor, and/or any other suitable sensors or combinations thereof.

The wearable device 104 may include a memory 110 as well as a processor 112. The memory 110 may store an operating system 110a capable of facilitating the functionalities as discussed herein, as well as other data 110b, an anomaly detection model 110c, a pattern dictionary encoder 110d, and a pattern dictionary 110e. Generally, the processor 112 may interface with the memory 110 to access/execute the operating system 110a, the other data 110b, the anomaly detection model 110c, the pattern dictionary encoder 110d, and the pattern dictionary 110e. The other data 110b may include a set of applications configured to facilitate the functionalities as discussed herein, and/or may include other relevant data, such as display formatting data, etc. For example, the processor 112 may access the operating system 110a in order to execute applications included as part of the other data 110b, such as a fitness application (not shown) configured to facilitate functionalities associated with enhancing anomaly detection using a pattern dictionary, as discussed herein. It should be appreciated that one or more other applications are envisioned.

Generally, the pattern dictionary encoder 110d may receive physiological data of the user 102, as collected by the set of sensors 108. Thereafter, the pattern dictionary encoder 110d may parse the physiological data using the pattern dictionary 110e to determine both a number of parsed phrases and a codelength corresponding to the physiological data. The number of parsed phrases may correspond to a number of distinct/unique phrases included in the physiological data collected by the set of sensors 108, and the codelength may correspond to an aggregate length or size (e.g., bits, bytes) of the physiological data. Of course, in certain aspects, the number of parsed phrases may correspond to the total number of parsed phrases (including redundant phrases) and/or any other suitable identification of the phrases included as part of the physiological data of the user 102. Additionally, in certain aspects, the codelength may correspond to the total length or size (e.g., bits, bytes) of all parsed phrases included in the physiological data, such that the codelength of each instance of a redundant phrase (e.g., repeated phrases in sequential physiological data) is included in the calculation performed by the pattern dictionary encoder 110d to determine the codelength.

The anomaly detection model 110c may be configured to output anomalous data indications that generally indicate whether or not the physiological data includes an anomalous data sequence (e.g., subsequence). As part of the analysis performed by the anomaly detection model 110c, the model 110c may receive the number of parsed phrases and the codelength parsed/generated by the pattern dictionary encoder 110d using the pattern dictionary 110e based on physiological data of a user 102. Using this data from the pattern dictionary encoder 110d, the anomaly detection model 110c may determine whether or not both/either of the number of parsed phrases and the codelength exceed respective thresholds. If the anomaly detection model 110c determines that either the number of parsed phrases or the codelength exceeds the respective threshold, the anomaly detection model 110c may output an anomalous data indication that indicates that the physiological data includes an anomalous sequence.

In certain aspects, the anomalous data indication may correspond to symptomatic and/or healthy periods of a user 102 wearing the wearable device 104 relative to a particular adverse health condition. In these aspects, the anomalous data indication may convey to a user 102 that the physiological data collected by the set of sensors 108 indicates that the user 102 is either currently symptomatic with an adverse health condition and/or that the physiological data of the user 102 is trending towards symptomatic levels of the adverse health condition. However, as previously mentioned, it is to be appreciated that the anomalous data indication may correspond to any suitable indication that the data input to the pattern dictionary encoder 110d, and thereafter, the anomaly detection model 110c includes an anomalous sequence and/or is otherwise anomalous.

Prior to performing analysis, however, the pattern dictionary encoder 110d may receive training data to train the pattern dictionary 110e. The training data may include training physiological data collected by the set of sensors 108, and input from the user 102 indicating a physical state of the user 102 corresponding to the training physiological data. The input may generally be a user 102 response to a prompt or otherwise question presented, for example, to the user 102 via a user interface of the wearable device 104. The pattern dictionary encoder 110d may periodically access/request/retrieve this training data collected by the set of sensors 108 and analyze the training physiological data and input to continually train/update the pattern dictionary 110e. When received, the pattern dictionary encoder 110d may analyze whether or not the input from the user indicates that the user 102 is healthy in the period of time corresponding to the training physiological data.

In response to the input indicating the user 102 was healthy during the period of time corresponding to the training physiological data, the pattern dictionary encoder 110d may parse the training physiological data to generate a set of parsed phrases from the training physiological data. Each parsed phrase generated from the training physiological data that is not represented in the pattern dictionary 110e (e.g., a new parsed phrase) may be added to the pattern dictionary 110e. As such, the pattern dictionary 110e may include each previously parsed phrase from all training physiological data sets wherein the user was healthy (e.g., no observed or predicted symptoms of an infection/illness based on the user's input). In this manner, should the pattern dictionary encoder 110d parse a new phrase from the physiological data of the user 102 received during active testing (e.g., outside of training) that is not included in the pattern dictionary 110e, then the new phrase may inherently represent that the user 102 is potentially symptomatic (e.g., one or more observed or predicted symptoms of an infection/illness) in some way.

In certain aspects, the server 106 may perform the training/updating of the pattern dictionary 110e. For example, the wearable device 104 may collect physiological data (e.g., via the set of sensors 108) of a user 102, and may apply the pattern dictionary encoder 110d, pattern dictionary 110e, and the anomaly detection model 110c to the physiological data to determine whether or not the physiological data includes an anomalous data sequence. The pattern dictionary encoder 110d may parse a new phrase from the physiological data, and the wearable device 104 may prompt the user 102 to provide input regarding the user's 102 current health status. If the user 102 indicates that the user 102 is healthy, then the wearable device 104 may store the new parsed phrase in memory 110 for eventual transmission to the server 106. The wearable device 104 may transmit the new parsed phrase to the server 106 when, for example, the user 102 removes the wearable device 104 in order to charge the device 104, such that the device 104 is not gathering new physiological data of the user 102. The server 106 may receive the new parsed phrase and proceed to update the pattern dictionary 110e that is stored on the server memory 120. Once updated, the server 106 may transmit the updated pattern dictionary to the wearable device 104 for future implementation as the pattern dictionary 110e.

As another example, the wearable device 104 may collect training physiological data of the user 102 prior to training the pattern dictionary 110e, such that the pattern dictionary 110e contains no entries of known parsed phrases corresponding to healthy periods of the user 102. The wearable device 104 may also collect input from the user 102 regarding whether or not the user 102 is healthy during the periods associated with the training physiological data. The wearable device 104 may transmit the training physiological data and the inputs to the server 106 when, for example, the user 102 removes the wearable device 104 in order to charge the device 104, such that the device 104 is not gathering new physiological data of the user 102. The server 106 may receive the training physiological data and the inputs and proceed to train the pattern dictionary 110e that is stored on the server memory 120 by inputting all unique/distinct parsed phrases parsed from the training physiological data (e.g., either by the pattern dictionary encoder 110d stored on the wearable device 104 and/or the server 106) that correspond to inputs indicating that the user 102 was healthy during the periods associated with the parsed phrases. Once trained, the server 106 may transmit the trained pattern dictionary to the wearable device 104 for future implementation as the pattern dictionary 110e.

In certain aspects, the server 106 may periodically update/train the pattern dictionary 110e based upon an aggregate pattern dictionary (not shown) of a plurality of users of similar wearable devices (e.g., crowdsourcing updates to the pattern dictionary 110e). The server 106 may utilize common parsed phrases from the plurality of users that are known to correspond to healthy periods in order to proactively train the pattern dictionary 110e for the user 102. In this manner, the pattern dictionary 110e may include more known parsed phrases corresponding to healthy periods than the wearable device 104 of the user 102 may have yet encountered by parsing just the physiological data of the user 102, thereby reducing the false positive rate of anomalous data indications indicating anomalous data sequences and user prompts to validate or otherwise indicate whether or not the user is healthy.

As an example of an active test (e.g., non-training) analysis sequence of the anomaly detection model 110c, if a user 102 is healthy and shows no physiological symptoms associated with an adverse health condition (e.g., elevated heart rate), then the anomaly detection model 110c may generate an anomalous data indication indicating that the user 102 is healthy (e.g., no sequence of the physiological data is anomalous). By contrast, if the user 102 is experiencing physiological symptoms associated with an adverse health condition, then the anomaly detection model 110c may generate an anomalous data indication indicating that the user 102 is symptomatic (e.g., at least one sequence of the physiological data is anomalous). In certain cases, a user 102 may not experience many or any prominent physiological symptoms associated with an adverse health condition, but the anomaly detection model 110c may analyze the physiological data collected by the set of sensors 108 and conclude that an anomalous data indication indicating that the user 102 is symptomatic applies to the physiological data of the user 102.

In any event, once the anomaly detection model 110c receives the parsed phrases and codelength from the pattern dictionary encoder 110d and pattern dictionary 110e and outputs the anomalous data indication, the model 110c may output the anomalous data indication for display and/or further analysis by the wearable device 104. Moreover, the processors 112 of the wearable device 104 may receive the anomalous data indication, interpret the indication, and may generate an alert for display to the user 120 via the user interface 118 of the wearable device 104. The processors 112 may include a set of instructions that are configured to interpret the anomalous data indication as, for example, indicative of the user 102 being symptomatic of a particular adverse health condition, generally symptomatic and/or otherwise unhealthy, healthy, and/or any other suitable health status or combinations thereof.

To illustrate, assume that the anomalous data indication indicates that the physiological data analyzed by the anomaly detection model 110c and pattern dictionary encoder 110d using the pattern dictionary 110e is substantially different from the training physiological data used to train/update the pattern dictionary 110e. For example, the physiological data may be substantially different from the training physiological data because the number of parsed phrases and/or the codelength of the physiological data greatly exceeds and/or otherwise fails to satisfy the respective threshold values that are based on the training physiological data. Thus, the anomaly detection model 110c may output the anomalous data indication as a numerical score (e.g., expressed as an integer value, percentage, ratio, etc.), a classification, and/or other suitable metric that suitably indicates that the number of parsed phrases and/or codelength of the physiological data greatly exceeds and/or otherwise fails to satisfy the respective threshold values. The processors 112 may receive the anomalous data indication, and apply pre-determined (e.g., rule-based) instructions that automatically associate the anomalous data indication with one or more of a plurality of potential alerts for presentation to the user 102. Further, both the anomalous data indication and/or the alert may be saved locally in the memory 110 and/or used as part of an application or platform executed on the wearable device 104 and/or the user device 132.

Generally, the anomaly detection model 110c may be a rules-based model that receives the number of parsed phrases and codelength from the pattern dictionary encoder 110d, and outputs the anomalous data indication(s) by comparing the number of parsed phrases and codelength values to the respective threshold values, as previously described. As an example, assume that the anomaly detection model 110c compares the number of parsed phrases and codelength values from physiological data of a user 102 to their respective threshold values, and determines that the number of parsed phrases exceeds the parsed phrase threshold by 5 and that the codelength exceeds the codelength threshold by 10%. In this example, the anomaly detection model 110c may determine that the physiological data is generally anomalous (e.g., contains anomalous data), and may proceed to identify anomalous data strings within the physiological data. To further this example, the anomaly detection model 110c may identify anomalous data strings by, for instance, identifying regions within the physiological data that have a high concentration of new parsed phrases (e.g., phrases that are not included in the pattern dictionary 110e) and/or that have a longer than average codelength relative to the codelength threshold. Once identified, the anomaly detection model 110c may output these anomalous data strings as part of the anomalous data indication.

However, in certain aspects, the anomaly detection model 110c may be an artificial intelligence (AI) based model trained with at least one AI algorithm. In these aspects, training of the anomaly detection model 110c involves training data analysis to configure weights of the anomaly detection model 110c used to predict and/or classify future received physiological data. The training may be performed locally by a user device (e.g., wearable device 104, user device 132); however, in some aspects, one or more processors of a server or a cloud-based computing platform (e.g., server 106) may receive a plurality of training data representing the healthy periods and/or symptomatic periods of respective users (e.g., training codelength values for each parsed phrase included in the pattern dictionary and a training number of parsed phrases from training physiological data) via a computer network (e.g., network 130). In such aspects, the server and/or the cloud-based computing platform may train the anomaly detection model 110c with the plurality of training data.

As previously mentioned, an AI based model, as described herein (e.g. anomaly detection model 110c), may be trained using a supervised machine learning program or algorithm. Generally, machine learning may involve identifying and recognizing patterns in existing data (such as generating anomalous data indications corresponding to physiological data received from a wearable device of a user) in order to facilitate making predictions or identification for subsequent data (such as using the model 110c on new physiological data in order to determine or generate anomalous data indications corresponding to the new physiological data received from the wearable device of the user). Machine learning model(s), such as the AI based model described herein for some aspects, may be created and trained based upon example data (e.g., "training data" and related user-specific data) inputs or data (which may be termed "features" and "labels") in order to make valid and reliable predictions for new inputs, such as testing level or production level data or inputs.

In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

However, in certain aspects, the AI based model may be trained using multiple supervised machine learning techniques, and may additionally or alternatively be trained using one or more unsupervised machine learning techniques. In unsupervised machine learning, the server, computing device, or otherwise processor(s), may be required to find its own structure in unlabeled example inputs, where, for example multiple training iterations are executed by the server, computing device, or otherwise processor(s) to train multiple generations of model until a satisfactory model, e.g., a model that provides sufficient prediction accuracy when given test level or production level data or inputs, is generated.

For example, in certain aspects, the AI based model may employ a support vector machine (SVM) algorithm, which may be a program that learns using two or more features or feature datasets (e.g., user-specific physiological data). The machine learning programs or algorithms may also include natural language processing, semantic analysis, neural networks, automatic reasoning, decision tree analysis, random forest analysis, K-Nearest neighbor analysis, naïve Bayes analysis, clustering, reinforcement learning, and/or other machine learning algorithms and/or techniques. In some aspects, the artificial intelligence and/or machine learning based algorithms may be included as a library or package executed on the server 106. For example, libraries may include the TENSORFLOW based library, the PYTORCH library, the SCIKIT-LEARN Python library, and/or a MAT-LAB library.

Regardless, training the AI based model (e.g., anomaly detection model 110c) may also comprise retraining, relearning, or otherwise updating models with new, or different, information, which may include information received, ingested, generated, or otherwise used over time. Moreover, in various aspects, the AI based model may be trained, by one or more processors (e.g., processor(s) 122 of server 106 and/or processor(s) of a computer user device, such as the wearable device 104 and/or the user device 132) with the plurality of training data of healthy periods and/or symptomatic periods (e.g., training codelength values for each parsed phrase included in the pattern dictionary and a training number of parsed phrases from training physiological data) of respective individuals. In these aspects, the AI based model may additionally be configured to generate/output respective anomalous data indications corresponding to each of the training physiological data of each respective individual included as part of the plurality of training data.

In any event, the memory 110 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others.

The wearable device 104 may further include a communication module 116 configured to communicate data via one or more networks 130. According to some aspects, the communication module 116 may include one or more transceivers (e.g., WWAN, WLAN, and/or WPAN transceivers) functioning in accordance with IEEE standards, 3GPP standards, or other standards, and configured to receive and transmit data via one or more external ports 114. For example, the communication module 116 may communicate with the server 106 via the network(s) 130.

The wearable device 104 may further include a user interface 118 configured to present information to the user 102 and/or receive inputs from the user 102. As shown in FIG. 1A, the user interface 118 may include a display screen 118a and I/O components 118b (e.g., ports, capacitive or resistive touch sensitive input panels, keys, buttons, lights, LEDs). According to some aspects, the user 102 may access the wearable device 104 via the user interface 118 to review warnings displayed as a result of outputs from the anomaly detection model 110c, physiological data collected by the set of sensors 108, make various selections, and/or otherwise interact with the wearable device 104.

In some aspects, the wearable device 104 may perform the functionalities as discussed herein as part of a "cloud" network or may otherwise communicate with other hardware or software components within the cloud to send, retrieve, or otherwise analyze data.

As illustrated in FIG. 1A, the wearable device 104 may communicate and interface with the server 106 via the network(s) 130. The server 106 may be associated with, for example, an entity that owns, operates, and/or manages a fitness application or platform and/or a medical services provider that maintains medical records for the user 102. In particular, the server 106 may include or support a web server configured to host a website that enables users to operate the fitness application or platform. Further, the server 106 may support a software application executable by the wearable device 104 (i.e., the wearable device 104 may interface with the server 106 in executing the software application). In certain aspects, the network(s) 130 may support any type of data communication via any standard or technology (e.g., GSM, CDMA, TDMA, WCDMA, LTE, EDGE, OFDM, GPRS, EV-DO, UWB, Internet, IEEE 802 including Ethernet, WiMAX, Wi-Fi, Bluetooth, and others).

The server 106 may include a memory 120 as well as a processor 122. The memory 120 may store an operating system 120a capable of facilitating the functionalities as discussed herein as well as other data 120b and the anomaly detection model 110c. Generally, the processor 122 may interface with the memory 120 to access/execute the operating system 120a, the other data 120b, the anomaly detection model 110c, the pattern dictionary encoder 110d, and the pattern dictionary 110e. The other data 120b may include data received from the wearable device 104, a set of applications configured to facilitate the functionalities as discussed herein, and/or may include other relevant data, such as display formatting data, etc. For example, the processor 122 may access the operating system 120a in order to execute applications included as part of the other data 120b, such as a fitness application (not shown) configured to facilitate functionalities associated with enhancing anomaly detection using a pattern dictionary, as discussed herein. It should be appreciated that one or more other applications are envisioned.

The memory 120 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. Further, the server 106 may be configured to interface with or support an external memory or storage (not shown) capable of storing various data, such as in one or more databases or other forms of storage. According to certain aspects, the external storage may store data or information associated with user 102 medical records, physiological data, and/or other suitable data corresponding to the systems and methods described herein. For example, the external storage may store heart rate data of the user 102.

The server 106 may further include a communication module 126 configured to communicate data via the network(s) 130. According to some aspects, the communication module 126 may include one or more transceivers (e.g., WWAN, WLAN, and/or WPAN transceivers) functioning in accordance with IEEE standards, 3GPP standards, or other standards, and configured to receive and transmit data via one or more external ports 124.

The server 106 may further include a user interface 128 configured to present information to a user and/or receive inputs from the user. As shown in FIG. 1A, the user interface 128 may include a display screen 128a and I/O components 128b (e.g., ports, capacitive or resistive touch sensitive input panels, keys, buttons, lights, LEDs). According to some aspects, the user 102 may access the server 106 via the user interface 128 to review information (e.g., alerts generated based on anomalous data indications output from the anomaly detection model 110c, physiological data collected by the set of sensors 108), make selections, and/or perform other functions.

In some aspects, the server 106 may perform the functionalities as discussed herein as part of a "cloud" network or may otherwise communicate with other hardware or software components within the cloud to send, retrieve, or otherwise analyze data. Moreover, although depicted as a single server 106 in FIG. 1A, it should be appreciated that the server 106 may be in the form of a distributed cluster of computers, servers, machines, or the like. In this implementation, the entity may utilize the distributed server(s) 106 as part of an on-demand cloud computing platform. Accordingly, when the wearable device 104 interfaces with the server 106, the wearable device 104 may actually interface with one or more of a number of distributed computers, servers, machines, or the like, to facilitate the described functionalities.

Additionally, the wearable device 104 may connect, through the network(s) 130, to the server 106 and a user device 132. The user device 132 may generally be any type of electronic device such as a mobile device (e.g., a smartphone), desktop computer, notebook computer, tablet, phablet, GPS (Global Positioning System) or GPS-enabled device, smart watch, smart glasses, smart bracelet, wearable electronic, PDA (personal digital assistant), pager, computing device configured for wireless communication, and/or the like. The user device 132 may execute or interface with an application or platform that enables the user 102 to view physiological data, medical records, etc. collected by the wearable device 104 and/or stored by the server 106. It will be appreciated that the user device 132 may also include the anomaly detection model 110c, pattern dictionary encoder 110d, pattern dictionary 110e, and may receive physiological data from the wearable device 104 in order to perform some/all of the functionality described herein.

Although two (2) electronic devices 104, 132 and one (1) server 106 are depicted in FIG. 1A, it should be appreciated that greater or fewer amounts are envisioned. For example, there may be multiple servers, each one associated with a different entity. Moreover, it is to be appreciated that a computer program product in accordance with an aspect may include a computer usable storage medium (e.g., standard random access memory (RAM), an optical disc, a universal serial bus (USB) drive, or the like) having computer-readable program code embodied therein, wherein the computer-readable program code may be adapted to be executed by the processors 112, 122 (e.g., working in connection with the respective operating systems 110a, 120a) to facilitate the functions as described herein. In this regard, the program code may be implemented in any desired language, and may be implemented as machine code, assembly code, byte code, interpretable source code or the like (e.g., via Golang, Python, Scala, C, C++, Java, Actionscript, Objective-C, Javascript, CSS, XML). In some aspects, the computer program product may be part of a cloud network of resources.

Figure 1B:
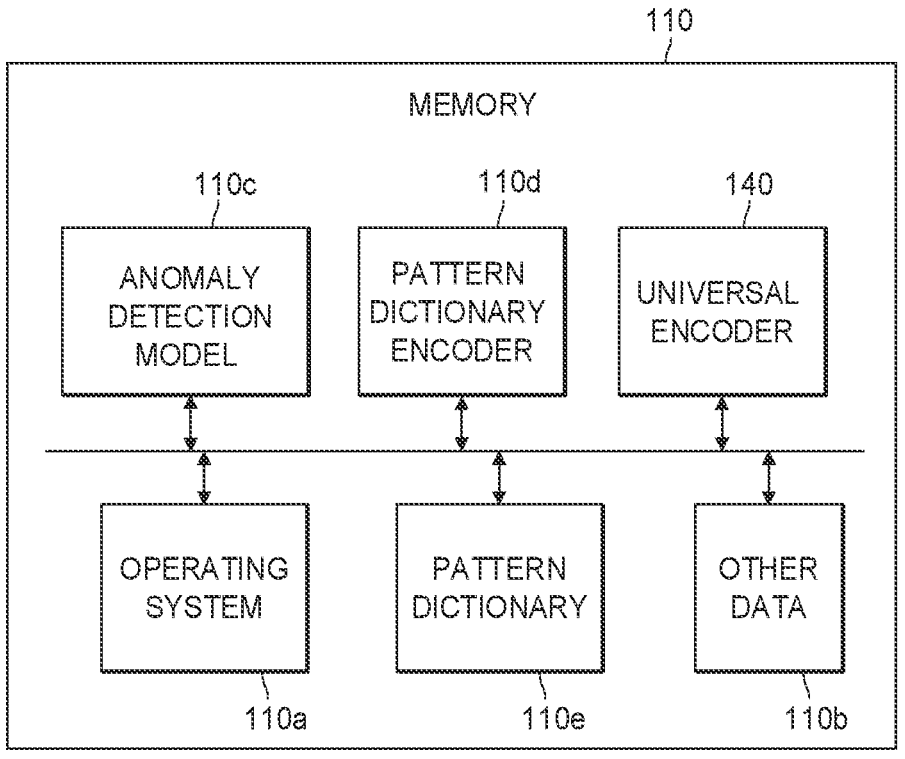
FIG. 1B illustrates an example memory including the anomaly detection model from the example system in FIG. 1A, in accordance with various aspects disclosed herein.

FIG. 1B illustrates the memory 110 including the anomaly detection model 110c from the example system 100 in FIG. 1A, in accordance with various aspects disclosed herein. It is to be understood that the memory 110 may also represent and/or be the memory 120 of the server 106 and/or the memory (not shown) of the user device 132 from the example system 100 in FIG. 1A.

The memory 110 includes the operating system 110a, the other data 110b, the anomaly detection model 110c, the pattern dictionary encoder 110d, the pattern dictionary 110e, and a universal encoder 140. Generally, and as previously discussed, the anomaly detection model 110c, the pattern dictionary encoder 110d, and the pattern dictionary 110e may receive and analyze physiological data of a user from sensors (e.g., set of sensors 108) of a wearable device (e.g., wearable device 104) to determine whether or not the physiological data collected by the wearable device is anomalous. However, as illustrated in FIG. 1B, the memory 110 may additionally include the universal encoder 140 to determine whether or not the physiological data collected by the wearable device 104 is atypical. As described above and herein, the anomaly detection provided in the present disclosure generally utilizes the complexity of the physiological data (e.g., the number of parsed phrases and the codelength) to determine whether or not the physiological data is anomalous. By contrast, the atypicality of the physiological data may be generally defined as the difference between the complexity of the physiological data encoded by the pattern dictionary encoder 110d and pattern dictionary 110e and the complexity of the physiological data encoded by the universal encoder 140.

The universal encoder 140 may include a non-trained data encoder (e.g., that does not utilize the pattern dictionary 110e) that may determine a number of parsed phrases and a codelength corresponding to the physiological data collected by the wearable device. Thus, the number of parsed phrases and the codelength determined by the universal encoder 140 may differ from the respective values determined by the pattern dictionary encoder 110d utilizing the pattern dictionary 110e. As an example, assume that, for a particular set of physiological data, the universal encoder 140 determines 10 parsed phrases and a codelength of 10 kB (kilobytes), and the pattern dictionary encoder 110d utilizing the pattern dictionary 110e determines 12 parsed phrases and a codelength of 12 kB. In this example, the processors (e.g., processors 112, 122) may determine that the difference between the number of parsed phrases and the codelength determined by the universal encoder 140 and the pattern dictionary encoder 110d utilizing the pattern dictionary 110e may be sufficiently large (e.g., exceeds or otherwise fails to satisfy an atypical threshold value) that the physiological data may qualify as "atypical". As a result, the processors may generate an alert for display to a user (e.g., user 102), store the physiological data in memory 110, transmit the physiological data to a server (e.g., server 106) for further storage and/or analysis, and/or any other suitable action or combinations thereof.

Figure 2:
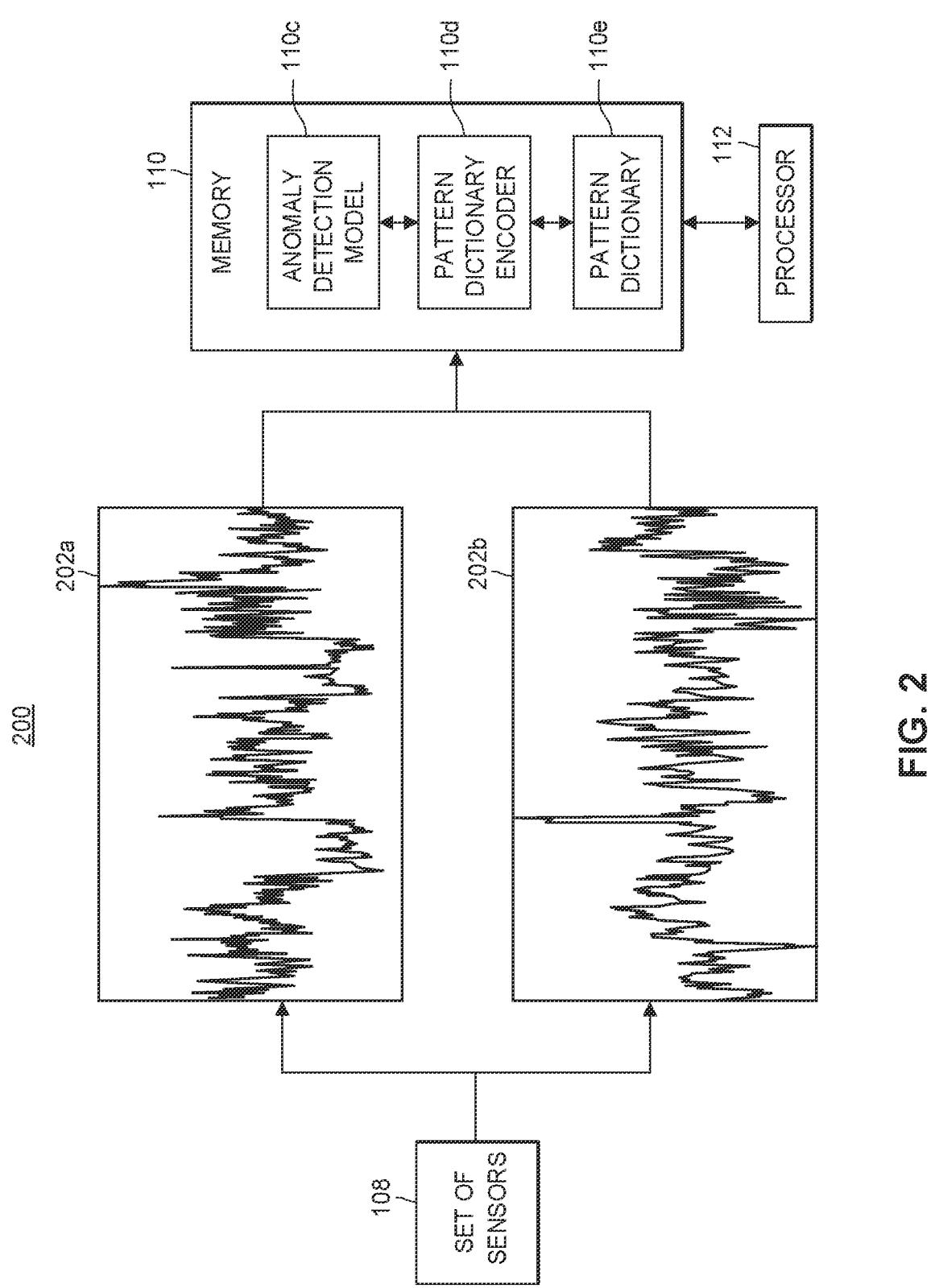
FIG. 2 is a flow diagram illustrating an example training sequence to train the anomaly detection model of FIG. 1A and the pattern dictionary of FIG. 1B, and in accordance with various aspects disclosed herein.

FIG. 2 is a flow diagram illustrating an example training sequence 200 to train the anomaly detection model 110c of FIG. 1A and the pattern dictionary 110e of FIG. 1B, and in accordance with various aspects disclosed herein. Generally, the example training sequence 200 includes the set of sensors 108 collecting physiological data 202a, 202b of a user (e.g., user 102), transmitting the physiological data 202a, 202b to the memory 110, and the processors 112 executing/accessing each of the pattern dictionary encoder 110d, the pattern dictionary 110e, and the anomaly detection model 110c to train the pattern dictionary 110e and the anomaly detection model 110c. The physiological data 202a may represent heart rate data of a user over any suitable period of time (e.g., minutes, hours, days, months, etc.), and the physiological data 202b may represent temperature data of the user over the same period of time. Of course, the example physiological data 202a, 202b may include data as collected by any sensor included as part of a wearable (e.g., the set of sensors 108). Regardless, heart rate data and temperature data are physiologic signals that, in conjunction with the techniques of the present disclosure, may be used to, for example, track disease progression, detect imminent symptom onset, and distinguish between positive and negative cases of common adverse health conditions.

Generally, the physiological data 202a, 202b may represent healthy heart rate and temperature data of the user, and the period of time over which the wearable device collects the physiological data 202a, 202b may be a training/calibration period for the pattern dictionary 110e and, in certain aspects, the anomaly detection model 110d. As such, the example training sequence 200 may also include an input from the user (not shown) indicating that the user is healthy during the period of time represented by the physiological data 202a, 202b. The user may be healthy during this training period because the user does not experience any symptoms associated with a common and/or otherwise adverse health condition.

During the training period represented by the physiological data 202a, 202b, the wearable device may acquire and utilize physiological data in order to train and/or otherwise calibrate the pattern dictionary 110e to include all parsed phrases that are parsed from the physiological data 202a, 202b. The processor 112 may access the memory 110 to retrieve the physiological data 202a, 202b, and apply the pattern dictionary encoder 110d to parse each phrase from the physiological data 202a, 202b that satisfies certain requirements for entry into the pattern dictionary 110e. For example, the requirements may include that the parsed phrases from the physiological data 202a, 202b have a sequence length (e.g., number of bits, characters, etc.) less than or equal to a maximum depth value associated with the pattern dictionary 110e.

Once the pattern dictionary encoder 110d successfully parses each phrase included in the physiological data 202a, 202b that satisfies the requirements for entry into the pattern dictionary 110e, the processor 112 may input each of the satisfactory parsed phrases into the pattern dictionary 110e. The processors 112 may also input the codelength associated with each parsed phrase generated by the pattern dictionary encoder 110d, and/or a probability of occurrence associated with each parsed phrase into the pattern dictionary 110e, thereby training the pattern dictionary 110e. The probability of occurrence may refer to the number of times the particular parsed phrase occurs in the physiological data 202a, 202b relative to the other parsed phrases of the same sequence length. Moreover, the probability of occurrence and/or the corresponding codelength may be updated each time the pattern dictionary 110e is updated, based on the overall number of times the particular parsed phrase occurs in the aggregate number of parsed data sequences that the pattern dictionary encoder 110d parses.

As an example, the training period represented by the physiological data 202a, 202b may begin 3-7 days prior to symptom onset, and may end at 0-2 days after symptom onset. However, it is to be understood that the training period represented by the physiological data 202a, 202b may begin/end at any suitable time relative to the onset of the user's adverse health condition, and may be of any suitable length (e.g., minutes, hours, days, months, etc.).

As a result of the example training sequence 200, the processor 112 establishes a user-specific baseline set of phrases included in physiological data corresponding to the user wearing the wearable device that are encapsulated within the trained pattern dictionary 110e. Thereafter, and as discussed herein, the wearable device may apply the trained pattern dictionary 110e to non-training (e.g., test) physiological data collected during a symptomatic period of an adverse health condition of the user to compare the baseline set of phrases to parsed phrases from the test physiological data. In this manner, the anomaly detection model 110c may accurately detect when a user has contracted an adverse health condition by, in part, determining that the number of parsed phrases from the test physiological data deviates significantly (e.g., more than the parsed phrase threshold) from the number of parsed phrases included in the trained pattern dictionary 110e.

Moreover, in certain aspects, the processors 112 may utilize the physiological data 202a, 202b, the pattern dictionary encoder 110d, and the trained pattern dictionary 110e to train the anomaly detection model 110c to output anomalous data indications. For example, the processors 112 may access the number of parsed phrases and codelength generated by the pattern dictionary encoder 110d and pattern dictionary 110e when applied to the physiological data 202a, 202b as well as the user input indicating that the user is healthy, and apply the number of parsed phrases and codelength to the anomaly detection model 110c. The anomaly detection model 110c may output an anomalous data indication corresponding to the physiological data 202a, 202b, which the processor 112 may compare with the input from the user indicating the relative health of the user.

For example, assume that the user input indicates that the user is healthy during the period of time represented by the physiological data 202a, 202b, and that the anomaly detection model 110c outputs an anomalous data indication based on the physiological data 202a, 202b (e.g., number of parsed phrases and codelength from the pattern dictionary encoder 110d and pattern dictionary 110e) indicating that the user is symptomatic of an adverse health condition. In this example, the processors 112 may determine that the anomaly detection model 110c incorrectly classified the physiological data 202a, 202b as symptomatic instead of healthy, and as a result, may adjust one or more weights of the anomaly detection model 110c, the parsed phrased threshold and/or the codelength threshold, and/or any other suitable parameters of the model 110c. Of course, the processor 112 may train the anomaly detection model 110c for any suitable period of time (e.g., several weeks/months) to properly train the model 110c to output anomalous data indications corresponding to the physiological data.

Figure 3A:
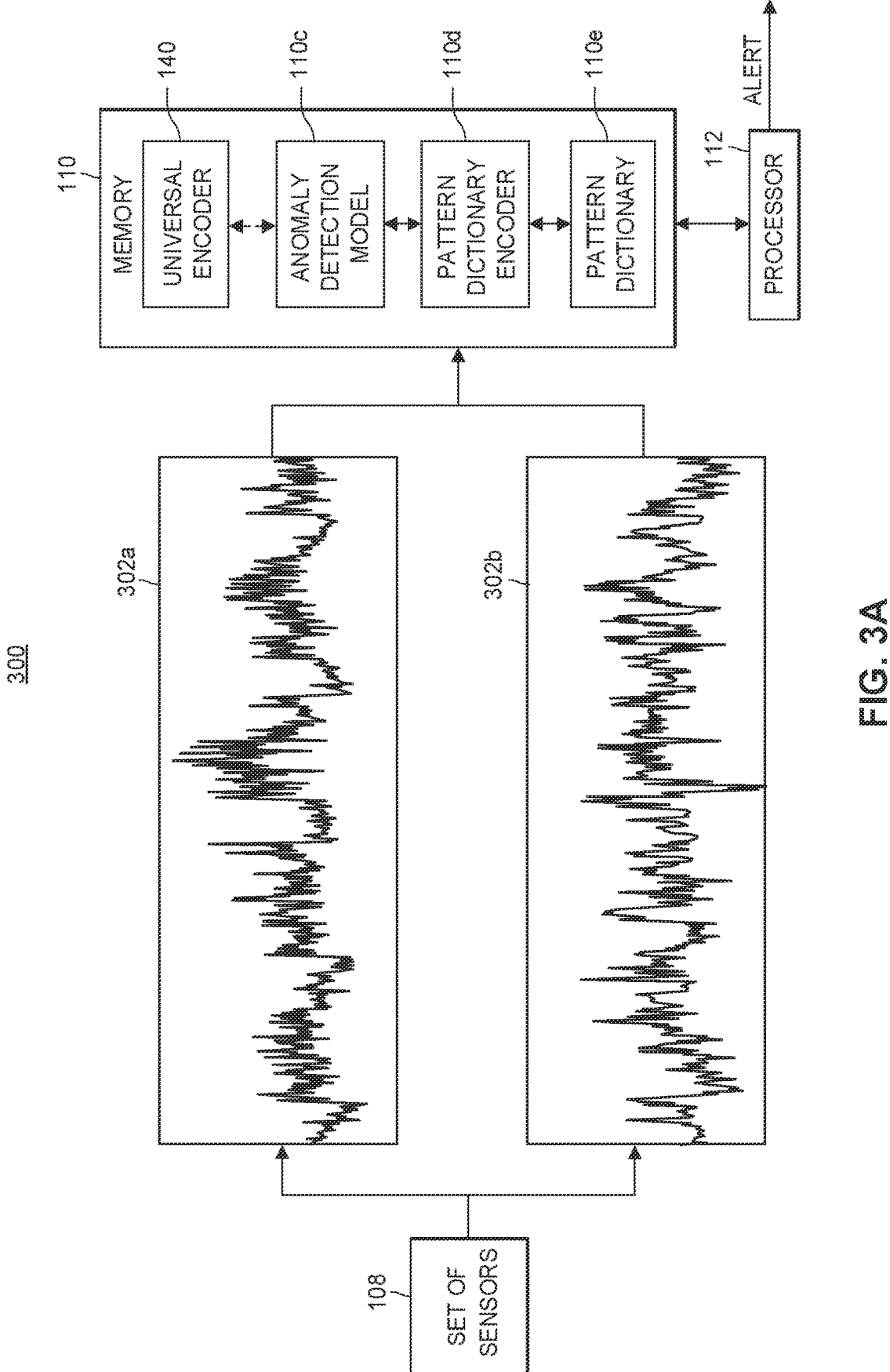
FIG. 3A is a flow diagram illustrating an example anomaly detection sequence configured to detect anomalous data sequences in test physiological data received by the anomaly detection model and the pattern dictionary encoder of FIG. 1A, in accordance with various aspects disclosed herein.

FIG. 3A is a flow diagram illustrating an example anomaly detection sequence 300 configured to detect anomalous data sequences in test physiological data 302a, 302b received by the anomaly detection model 110c and the pattern dictionary encoder 110d of FIG. 1A, in accordance with various aspects disclosed herein. Generally, the test physiological data 302a, 302b may represent a symptomatic period, during which, the user may develop/experience symptoms as a result of an adverse health condition. More specifically, the test physiological data 302a may be heart rate data of the user during the symptomatic period, and the test physiological data 302b may be temperature data of the user during the symptomatic period. The set of sensors 108 may collect and store the physiological data 302a, 302b for a few days/weeks to determine whether or not a user has contracted an adverse health condition. Of course, the set of sensors 108 may collect and/or store physiological data for any suitable length of time, such as minutes, hours, days, weeks, months, years, etc.

During the symptomatic period represented by the test physiological data 302a, 302b, the set of sensors 108 may acquire the test physiological data 302a, 302b and may thereafter (or during) transmit the physiological data 302a, 302b to the memory 110 for storage/analysis to determine whether or not the user has contracted an adverse health condition by executing/applying the pattern dictionary encoder 110d, the pattern dictionary 110e, the anomaly detection model 110c, and optionally, the universal encoder 140. Upon receipt of the test physiological data 302a, 302b, the processors 112 may apply the pattern dictionary encoder 110d to the test physiological data 302a, 302b to generate a number of parsed phrases and a codelength value for the physiological data 302a, 302b based on the pattern diction- ary 110e. The processors 112 may utilize these two values when subsequently executing the anomaly detection model 110c.

The processors 112 may execute the anomaly detection model 110c to determine whether or not the number of parsed phrases and/or the codelength value exceeds the respective threshold value (e.g., parsed phrase threshold, codelength threshold). In the event that the anomaly detec- tion model 110c determines that one or both of the number of parsed phrases and/or the codelength value exceeds or otherwise fails to satisfy the respective threshold value, the model 110c may output an anomalous data indication indi- cating that the physiological data 302a, 302b includes an anomalous data sequence. However, if the anomaly detec- tion model 110c determines that neither of the number of parsed phrases nor the codelength value exceeds or other- wise fails to satisfy the respective threshold value, the model 110c may output an anomalous data indication indicating that the physiological data 302a, 302b does not include an anomalous data sequence.

In any event, the processors 112 may also execute the universal encoder 140 in order to determine whether or not the physiological data 302a, 302b is atypical. The universal encoder 140 may parse the physiological data 302a, 302b to determine a codelength value that the processors 112 may compare to the codelength value determined by the pattern dictionary encoder 110d. The codelength value determined by the universal encoder 140 may be a more general encoding of the physiological data 302a, 302b because the universal encoder 140 does not include and/or otherwise utilize the trained pattern dictionary 110e. As a result, if the codelength determined by the universal encoder 140 is less than the codelength determined by the pattern dictionary encoder 110d and the trained pattern dictionary 110e, the processors 112 may determine (via, e.g., the anomaly detec- tion model 110c) that the physiological data 302a, 302b includes an atypical sequence.

Based upon the outputs from the pattern dictionary encoder 110d, the anomaly detection model 110c, and optionally, the universal encoder 140, the processors 112 may generate an alert. The alert may generally correspond to whether or not the physiological data 302a, 302b includes an anomalous sequence, an atypical sequence, and/or whether the user's input is required/desired or any combinations thereof. For example, the processors 112 may output an alert that indicates that the physiological data 302a, 302b poten- tially includes an anomalous data sequence and requesting the user's input to confirm whether or not the user was healthy during the time period associated with the physi- ological data 302a, 302b.

Figure 3B:
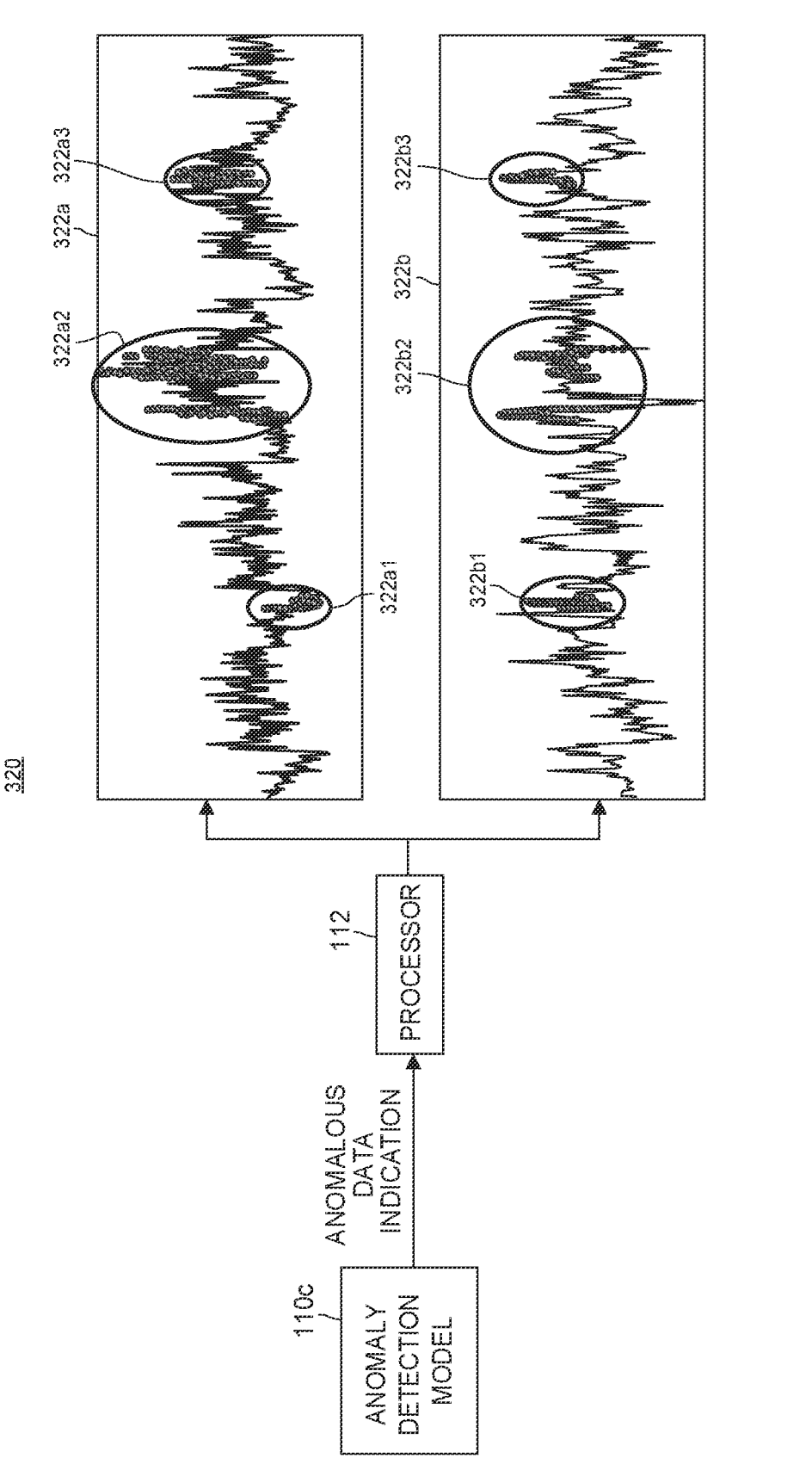
FIG. 3B is a flow diagram illustrating an example alert output as a result of the anomaly detection sequence of FIG. 3A, in accordance with various aspects disclosed herein.

As part of these alerts, and/or as otherwise generated by the anomaly detection model 110c, FIG. 3B is a flow diagram illustrating an example alert output 320 as a result of the anomaly detection sequence 300 of FIG. 3A, in accordance with various aspects disclosed herein. Generally, the physiological data outputs 322a, 322b includes the heart rate data of the user (e.g., user 102) and the temperature data of the user during the symptomatic period. As illustrated in FIG. 3B, the anomaly detection model 110c may determine that the physiological data 322a, 322b includes anomalous data sequences (e.g., represented as patterned circles in the anomalous areas 322a1-3 and 322b1-3). As a result, the anomaly detection model 110c may output an anomalous data indication indicating that the physiological data 322a, 322b includes anomalous data sequences, and the indication may further indicate the data sequences within the physi- ological data 322a, 322b that are anomalous.

Using the anomalous data indication, the processors 112 may generate a graphical rendering of the physiological data 322a, 322b that includes specific indications of the anoma- lous data sequences (e.g., represented as patterned circles in the anomalous areas 322a1-3 and 322b1-3). These graphical renderings may be displayed on a user interface (e.g., user interface 118) for presentation to a user, along with a description of the anomalous data sequences, as discussed herein. As such, these graphical renderings may be displayed to a user as part of an alert presented to a user indicating that the physiological data 322a, 322b is and/or includes an anomalous data sequence.

It is to be appreciated that the anomaly detection model 110c may output an anomalous data indication indicating that physiological data collected by the wearable device is non-anomalous (e.g., the user is healthy) despite the fact that an individual physiological parameter may include an anomalous data sequence. For example, assume that the anomaly detection model 110c identifies one small anoma- lous data sequence within heart rate physiological data of a user throughout a first time period represented by the heart rate physiological data. However, further assume that the anomaly detection model 110c does not detect any anoma- lous data sequences within temperature physiological data of the user throughout the first time period. In this example, the anomaly detection model 110c may output an anomalous data indication indicating that the user is non-symptomatic over the first time period despite the detection of the one small anomalous data sequence within the heart rate physi- ological data during the first period.

Moreover, while the examples provided above in refer- ence to FIGS. 2, 3A, and 3B describe particular instances of the anomaly detection model 110c, pattern dictionary encoder 110d, universal encoder 140, and/or the processors 112 calculating and/or determining values using specific physiological data (e.g., heart rate data and temperature data), it is to be understood that the set of sensors 108 may collect, and the anomaly detection model 110c, pattern dictionary encoder 110d, universal encoder 140, and/or the processors 112 may utilize any suitable physiological data as part of any suitable calculation or determination. Further, each of the example data/outputs illustrated in reference to FIGS. 2, 3A, and 3B may additionally or alternatively be generated and/or rendered based on calculations/determinations performed by a server (e.g., server 106) or a user device (e.g., wearable device 104, user device 132).

FIG. 4 illustrates an example method 400 for enhancing anomaly detection using a pattern dictionary, in accordance various aspects disclosed herein. For ease of discussion, many of the various actions included in the method 400 are described herein as performed by or with the use of a wearable device (e.g., wearable device 104). However, it is to be appreciated that the various actions included in the method 400 may be performed by, for example, a wearable device (e.g., wearable device 104), a user device (e.g., user device 132), a server (e.g., server 106), and/or other suitable processors or combinations thereof.

In any event, the method 400 may include receiving, at one or more processors from a wearable device, physiological data of a user (block 402). Generally, and as described herein, the physiological data of the user may comprise any suitable data, such as data collected by sensors of a wearable device (e.g., the set of sensors 108). For example, the physiological data may include multi-channel inputs from the wearable device (e.g., wearable device 104) that include any suitable number of mixed signals including blood pressure, electrodermal activity, accelerometer activity, and/or the like.

In certain aspects, the physiological data of the user includes at least one of: (i) a heart rate of the user, (ii) a temperature of the user, (iii) a blood pressure of the user, (iv) an electro dermal activity level of the user, (v) an inertial measurement unit (IMU) value of the user, or (vi) a blood oxygen level of the user. Thus, in these aspects, the set of sensors 108 of the wearable device 104 may include any combination of the previously mentioned sensors, such as the heart rate sensor 108a, the motion sensor(s) 108b (e.g., an IMU, an altimeter, a GPS, and EDA sensor), the temperature sensors 108c, a UV sensor, a gesture sensor, an ECG sensor, a proximity sensor, a bioimpedance sensor, a pulse oximeter (SpO2) sensor, an ambient light sensor, and/or any other suitable sensors or combinations thereof. Of course, it should be appreciated that the physiological data of the user may include any suitable signal measured by the wearable device (e.g., wearable device 104).

The method 400 further includes parsing, by applying a pattern dictionary encoder using a pattern dictionary, the physiological data into a set of parsed phrases having a number of parsed phrases (block 404). Each parsed phrase may represent a respective subsequence of the physiological data. Generally, the pattern dictionary encoder may parse the physiological data into subsequences that are included and/or otherwise recognized as part of the trained pattern dictionary. If the pattern dictionary encoder identifies and/or otherwise encounters a particular subsequence of the physiological data that is not included within the trained pattern dictionary, then the pattern dictionary encoder may perform a suitable action, such as not encoding the unrecognized subsequence, flagging the unrecognized subsequence to be sent to a server (discussed herein), and/or any other suitable action. In this manner, the pattern dictionary encoder may identify and parse all recognized subsequences within the physiological data utilizing the trained pattern dictionary.

In some aspects, prior to parsing the physiological data, the one or more processors (e.g., processors 112) may receive, from the sensors of the wearable device (e.g., set of sensors 108) a training data sequence corresponding to physiological signals of the user and an input from the user indicating a healthy physical condition of the user that is associated with the training data sequence. In these aspects, the one or more processors may apply the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence. Further, the one or more processors may input the training codelength value for each parsed phrase included in the pattern dictionary and the training number of parsed phrases into the anomaly detection model to train the anomaly detection model to output anomalous data indications.

To illustrate, assume that a wearable device of a user collects physiological data of the user (e.g., heart rate data and temperature data) during a first period (e.g., a training period), and the wearable device prompts the user to indicate whether or not the user was healthy during the first period. Further assume that the user indicates that the user was healthy during the first period, and that the processors use the physiological data to train the pattern dictionary by including all parsed subsequences up to a certain size (e.g., a maximum depth value) in the pattern dictionary. The processors may further use the number of parsed phrases included in the now trained pattern dictionary along with the codelength used to describe the physiological data to train the anomaly detection model to associate/correlate these number of parsed phrases and codelength values with a healthy (e.g., non-anomalous, normal) sequence of physiological data, as indicated by the user's input. Similarly, the wearable device may train the anomaly detection model using the number of parsed phrases and codelength values corresponding to a second set of physiological data collected by the wearable device in the event that a user indicates feeling unhealthy/symptomatic during a second period associated with the second set of physiological data.

In certain aspects, each parsed phrase included in the pattern dictionary and each parsed phrase included in the set of parsed phrases has a sequence length less than or equal to a maximum depth value associated with the pattern dictionary. Moreover, in some aspects, the pattern dictionary encoder may parse the physiological data into the set of parsed phrases by iteratively adjusting a string length and an initial string character of the physiological data that is analyzed by the pattern dictionary encoder until all subsequences comprising the physiological data that have a respective string length less than or equal to the maximum depth value are analyzed.

For example, the pattern dictionary encoder may parse the physiological data by analyzing a particular data sequence window that includes a predetermined number of bits of data. Within this particular data sequence window, the pattern dictionary encoder may iteratively parse the physiological data by analyzing each phrase within the window having a string length of 2 bits and a different initial string character, and incrementally increasing the string length until it reaches the maximum depth value (e.g., 3 bits, 4 bits, etc.) while analyzing each phrase within the window with different initial string characters for each string length.

The method 400 may further include determining, by the pattern dictionary encoder, a codelength corresponding to the physiological data based on the set of parsed phrases (block 406). The anomaly detection model (e.g., anomaly detection model 110*c*) may then compare (i) the number of parsed phrases to a parsed phrase threshold, and (ii) the codelength to a codelength threshold (block 408). Responsive to the number of parsed phrases exceeding the parsed phrase threshold or the codelength exceeding the codelength threshold, the anomaly detection model may output an anomalous data indication (block 410).

In certain aspects, the codelength is a first codelength, and the one or more processors (e.g., processors 112) may execute a universal encoder (e.g., universal encoder 140) to determine a second codelength corresponding to the physiological data. Further, the anomaly detection model may compare the first codelength to the second codelength to determine a codelength deviation. Responsive to the codelength deviation exceeding a deviation threshold the one or more processors may generate an alert indicating that the physiological data includes an atypical sequence/subsequence.

The method 400 may also include the one or more processors (e.g., processors 112) generating an alert for display on a user interface (e.g., user interface 118) indicating the anomalous data indication (block 412). Generally, the alert may indicate whether or not the anomaly detection model output an anomalous data indication indicating that the physiological data included an anomalous/atypical data sequence. For example, the alert may provide a user with an indication that the physiological data collected by the sensors (e.g., the set of sensors 108) included an anomalous data sequence, and as a result, the user should seek medical advice/attention. Alternatively, the alert may indicate to the user that the most recent physiological data collected by the sensors indicates that the user is healthy, and that the user should continue healthy living habits (e.g., exercise, vitamins, etc.). The user interface may be an integrated component of the wearable device (e.g., wearable device 104) and/or the wearable device may transmit the alert to a separate device (e.g., user device 132) for display on a user interface of the separate device.

In certain aspects, the one or more processors may transmit to a server (e.g., server 106) via a network (e.g., network 130) the pattern dictionary, the set of parsed phrases, and an indication of whether or not the one or more processors generated the alert. The server may analyze the set of parsed phrases to identify a new parsed phrase that is not included in the pattern dictionary. Responsive to determining that the indication indicates that the one or more processors did not generate the alert, the server may update the pattern dictionary by including the new parsed phrase in the pattern dictionary. The server may then transmit the pattern dictionary including the new parsed phrase to the one or more processors via the network. As previously mentioned, the pattern dictionary encoder may parse the new phrase that is not included in the pattern dictionary and/or may generate an indication that a phrase included in the physiological data is not included in the pattern dictionary to direct the server to the new phrase in the physiological data. Additionally, or alternatively, the server may re-parse all and/or a portion of the physiological data to identify the new parsed phrase, and thereby update the pattern dictionary by including the new parsed phrase.

Of course, in some instances, the anomaly detection model may output an anomalous data indication regardless of whether or not either the number of parsed phrases and/or the codelength exceed their respective thresholds (e.g., indicating that the model does not identify any anomalous/atypical data sequences in the analyzed physiological data), and as a result, the one or more processors may generate the alert. In these instances, the one or more processors may also send the pattern dictionary, the set of parsed phrases, and the indication of whether or not the one or more processors generated the alert to the server for analysis.

In certain aspects, the server may receive, via the network (e.g., network 130), a plurality of respective physiological data corresponding to a plurality of respective individuals. Included as part of the plurality of respective physiological data, a respective physiological data may include a respective new parsed phrase relative to the pattern dictionary of the user (e.g., user 102). For example, the server (e.g., server 106) may be a central server for the particular type of wearable device (e.g., wearable device 104), and may collect/aggregate physiological data corresponding to hundreds/thousands of users of the particular type of wearable device. The central server may receive the respective new parsed phrase from a respective user of a device, and may determine that the respective new parsed phrase should be included as part of some/all users' pattern dictionaries (e.g., pattern dictionary 110*e*) as a healthy physiological data sequence.

Accordingly, in these aspects, the server may update the pattern dictionary by including the respective new parsed phrase in the pattern dictionary. The server may then transmit the pattern dictionary including the respective new parsed phrase to the one or more processors via the network. The server may periodically perform these universal updates at any suitable frequency (e.g., every day, every week, every month, etc.). Further, the server may also determine that a respective parsed phrase universally included in each pattern dictionary should be removed, and may remove the respective parsed phrase from the pattern dictionary during a subsequent connection between the wearable device (e.g., wearable device) and the server. In either case, if the server determines that a respective parsed phrase should be removed/included from/in the pattern dictionary while the user (e.g., user 102) is currently wearing the wearable device, the server may wait to remove/include the pattern from/in the pattern dictionary until the user removes the wearable device (e.g., to charge the battery of the wearable device) and/or when the wearable device is otherwise not collecting physiological data of the user.

Figures 5A, 5B:
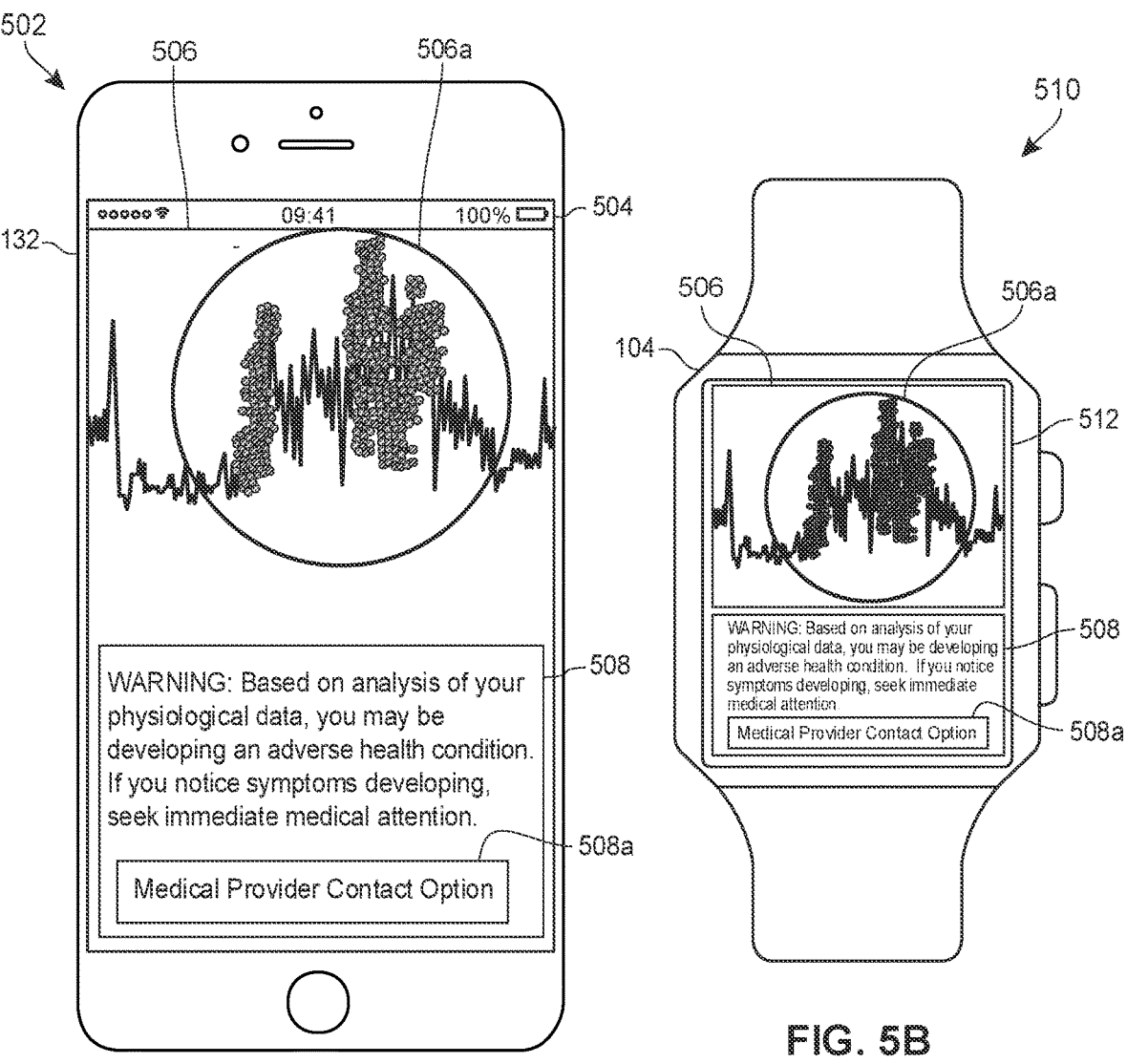
FIG. 5A illustrates an example user interface as rendered on a display screen of a user device, in accordance with various aspects disclosed herein.
FIG. 5B illustrates another example user interface as rendered on a display screen of a wearable device of the user, in accordance with various aspects disclosed herein.

When displaying alert, predictions, recommendations, and/or other outputs, the wearable device may provide displays similar to those presented in FIGS. 5A and 5B. FIG. 5A illustrates an example user interface 502 as rendered on a display screen of a user device (e.g., user device 132). For example, as shown in the example of FIG. 5A, the user interface 502 may be implemented or rendered via an application (app) executing on the user device 132. The user interface 502 may be implemented or rendered via a native app executing on the user device 132.

In the example of FIG. 5A, the user device 132 is a user device as described for FIG. 1A, e.g., where 132 is illustrated as an APPLE iPhone that implements the APPLE iOS operating system and that has display screen 504. The user device 132 may execute one or more native applications (apps) on its operating system, and such native apps may be implemented or coded (e.g., as computing instructions) in a computing language (e.g., SWIFT) executable by the user device 132 operating system (e.g., APPLE iOS) by the processor of user device 132. Additionally, or alternatively, the user interface 502 may be implemented or rendered via a web interface, such as via a web browser application, e.g., Safari and/or Google Chrome app(s), or other such web browser or the like.

As shown in the example of FIG. 5A, the user interface 502 comprises a graphical representation 506 (e.g., a portion of heart rate physiological data 322a) of a user's heart rate that includes an anomalous data sequence (e.g., represented as patterned circles in the anomalous area 506a). The graphical representation 506 may comprise physiological data of the user (or graphical representations thereof), as described herein. In the example of FIG. 5A, the graphical representation 506 is annotated with one or more graphics or textual rendering(s) (e.g., the patterned circles in anomalous area 506a) corresponding to the anomalous data sequence identifiable within the graphical representation 506. Additionally, any suitable graphics, colors, scores, patterns, and/or other renderings may be annotated or overlaid on top of the graphical representation 506 to highlight and/or otherwise draw the user's attention to the feature(s) of interest within the representation 506. In the example of FIG. 5A, the anomalous data sequence represented by the patterned circles in anomalous area 506a indicate an anomalous/atypical pattern in the user's heart rate, and may correspondingly indicate other physiological symptoms, as described herein.

The user interface 502 may also include or render a user-specific message 508 based on the data presented in the graphical representation 506. In the embodiment of FIG. 5A, the user-specific message 508 comprises an alert to the user designed to provide a brief description of the anomalous data indication output by the anomaly detection model (e.g., anomaly detection model 110c). As shown in the example of FIG. 5A, the message 508 indicates to a user that based on the analysis of the user's physiological data, the user may be developing an adverse health condition. Accordingly, the message 508 suggests that if the user notices symptoms developing, that the user should seek immediate medical attention.

In certain instances, and as previously mentioned, the one or more processors (e.g., processors 112) may determine a specific condition corresponding to the anomalous data sequence(s) identified by the anomaly detection model. Thus, the user-specific message 508 may also include a specific diagnosis corresponding to a particular adverse health condition, and may also include specific recommended behaviors/remedies to alleviate the user's symptoms. For example, the user-specific message 508 may alert a user that they may develop symptoms associated with the flu, and the message 508 may accordingly suggest that the user not over-exert themselves, get plenty of sleep, and remain well hydrated.

The user-specific message 508 may also include or render a medical provider contact option 508a, which may be a selectable UI button configured to provide the user with contact options for various medical providers in response to receiving input (e.g., selection) from the user. For example, a user may select the medical provider contact option 508a, and the application may retrieve and display phone numbers, websites, instant chat, telemedicine links, email addresses, and/or any other suitable contact option that a user may utilize to contact a medical provider.

Similarly, FIG. 5B illustrates another example user interface 510 as rendered on a display screen of a wearable device of the user (e.g., wearable device 104). The example user interface 510 includes the graphical representation 506 (e.g., a portion of heart rate physiological data 322a) of a user's heart rate that includes an anomalous data sequence (e.g., represented as patterned circles in the anomalous area 506a), the user-specific message 508, and the medical provider contact option 508a. Of course, the wearable device

104 may display each of the representation 506, the message 508, and the contact option 508a in a different format and/or rendering layout than the user device 132 due to dimensional differences of the respective display screens 504, 512.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A method for enhancing anomaly detection using a pattern dictionary, the method comprising:

receiving, at one or more processors from a wearable device, physiological data of the user;

parsing, by applying a pattern dictionary encoder using a pattern dictionary, the physiological data into a set of parsed phrases having a number of parsed phrases, wherein each parsed phrase represents a respective subsequence of the physiological data;

determining, by the pattern dictionary encoder, a codelength corresponding to the physiological data based on the set of parsed phrases;

comparing, by an anomaly detection model, (i) the number of parsed phrases to a parsed phrase threshold, and (ii) the codelength to a codelength threshold;

responsive to the number of parsed phrases exceeding the parsed phrase threshold or the codelength exceeding the codelength threshold, outputting, by the anomaly detection model, an anomalous data indication; and generating, by the one or more processors, an alert for display on a user interface indicating the anomalous data indication.

2. The method of claim 1, wherein the codelength is a first codelength, and the method further comprises:

determining, by applying a universal encoder, a second codelength corresponding to the physiological data;

comparing, by the anomaly detection model, the first codelength to the second codelength to determine a codelength deviation; and responsive to the codelength deviation exceeding a deviation threshold, generating, by the one or more processors, the alert.

3. The method of claim 1, further comprising:

receiving, from the wearable device, a training data sequence corresponding to physiological signals of the user and an input from the user indicating a healthy physical condition of the user that is associated with the training data sequence;

applying, by the one or more processors, the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence; and inputting, by the one or more processors, the training codelength value for each parsed phrase included in the pattern dictionary and the training number of parsed phrases into the anomaly detection model to train the anomaly detection model to output anomalous data indications.

4. The method of claim 3, wherein each parsed phrase included in the pattern dictionary and each parsed phrase included in the set of parsed phrases has a sequence length less than or equal to a maximum depth value associated with the pattern dictionary.

5. The method of claim 3, further comprising:

receiving, at a server from the one or more processors via a network, the pattern dictionary, the set of parsed phrases, and an indication of whether or not the one or more processors generated the alert;

analyzing, by the server, the set of parsed phrases to identify a new parsed phrase that is not included in the pattern dictionary;

responsive to determining that the indication indicates that the one or more processors did not generate the alert, updating, by the server, the pattern dictionary by including the new parsed phrase in the pattern dictionary; and transmitting, from the server to the one or more processors via the network, the pattern dictionary including the new parsed phrase.

6. The method of claim 5, further comprising:

receiving, at the server via the network, a plurality of respective physiological data corresponding to a plurality of respective individuals, wherein a respective physiological data of the plurality of respective physiological data includes a respective new parsed phrase;

updating, by the server, the pattern dictionary by including the respective new parsed phrase in the pattern dictionary; and transmitting, to the one or more processors from the server via the network, the pattern dictionary including the respective new parsed phrase.

7. The method of claim 1, further comprising:

parsing, by applying the pattern dictionary encoder, the physiological data into the set of parsed phrases by iteratively adjusting a string length and an initial string character of the physiological data that is analyzed by the pattern dictionary encoder until all subsequences comprising the physiological data that have a respective string length less than or equal to a maximum depth value are analyzed.

8. A non-transitory computer-readable storage medium having stored thereon a set of instructions, executable by at least one processor, for enhancing anomaly detection using a pattern dictionary, the instructions comprising:

instructions for receiving, from a wearable device, physiological data of the user;

instructions for parsing, by applying a pattern dictionary encoder using a pattern dictionary, the physiological data into a set of parsed phrases having a number of parsed phrases, wherein each parsed phrase represents a respective subsequence of the physiological data;

instructions for determining, by the pattern dictionary encoder, a codelength corresponding to the physiological data based on the set of parsed phrases;

instructions for comparing, by an anomaly detection model, (i) the number of parsed phrases to a parsed phrase threshold, and (ii) the codelength to a codelength threshold;

instructions for, responsive to the number of parsed phrases exceeding the parsed phrase threshold or the codelength exceeding the codelength threshold, outputting, by the anomaly detection model, an anomalous data indication; and instructions for generating an alert for display on a user interface indicating the anomalous data indication.

9. The non-transitory computer-readable storage medium of claim 8, wherein the codelength is a first codelength, and the instructions further comprise:

instructions for determining, by applying a universal encoder, a second codelength corresponding to the physiological data;

instructions for comparing, by the anomaly detection model, the first codelength to the second codelength to determine a codelength deviation; and instructions for, responsive to the codelength deviation exceeding a deviation threshold, generating the alert.

10. The non-transitory computer-readable storage medium of claim 8, wherein the instructions further comprise:

instructions for receiving, from the wearable device, a training data sequence corresponding to physiological signals of the user and an input from the user indicating a healthy physical condition of the user that is associated with the training data sequence;

instructions for applying the pattern dictionary encoder to the training data sequence to generate (i) the pattern dictionary, (ii) a training codelength value for each parsed phrase included in the pattern dictionary, and (iii) a training number of parsed phrases generated by the pattern dictionary encoder based on the training data sequence; and instructions for inputting the training codelength value for each parsed phrase included in the pattern dictionary and the training number of parsed phrases into the anomaly detection model to train the anomaly detection model to output anomalous data indications.

11. The non-transitory computer-readable storage medium of claim 10, wherein each parsed phrase included in the pattern dictionary and each parsed phrase included in the set of parsed phrases has a sequence length less than or equal to a maximum depth value associated with the pattern dictionary.

12. The non-transitory computer-readable storage medium of claim 8, wherein the instructions further comprise:

instructions for parsing, by applying the pattern dictionary encoder, the physiological data into the set of parsed phrases by iteratively adjusting a string length and an initial string character of the physiological data that is analyzed by the pattern dictionary encoder until all subsequences comprising the physiological data that have a respective string length less than or equal to a maximum depth value are analyzed.

\* \* \* \* \*